United States Patent
Papile

(10) Patent No.: US 11,260,378 B2
(45) Date of Patent: Mar. 1, 2022

(54) CATALYST SYSTEM AND PROCESS FOR PRODUCING BISPHENOL-A

(71) Applicant: BADGER LICENSING LLC, Boston, MA (US)

(72) Inventor: Christopher Papile, Cambridge, MA (US)

(73) Assignee: BADGER LICENSING LLC, Boston, MA (US)

( * ) Notice: Subject to any disclaimer, the term of this patent is extended or adjusted under 35 U.S.C. 154(b) by 84 days.

(21) Appl. No.: 16/607,494

(22) PCT Filed: Apr. 18, 2018

(86) PCT No.: PCT/US2018/028082
§ 371 (c)(1),
(2) Date: Oct. 23, 2019

(87) PCT Pub. No.: WO2018/200278
PCT Pub. Date: Nov. 1, 2018

(65) Prior Publication Data
US 2020/0047170 A1    Feb. 13, 2020

Related U.S. Application Data

(60) Provisional application No. 62/489,262, filed on Apr. 24, 2017.

(51) Int. Cl.
*C07C 39/16* (2006.01)
*B01J 31/00* (2006.01)
*B01J 31/10* (2006.01)
*B01J 31/02* (2006.01)

(52) U.S. Cl.
CPC ........... *B01J 31/10* (2013.01); *B01J 31/0217* (2013.01); *B01J 2231/347* (2013.01); *C07C 39/16* (2013.01)

(58) Field of Classification Search
CPC ....... C07C 39/16; B01J 31/10; B01J 31/0217; B01J 2231/347
See application file for complete search history.

(56) References Cited

U.S. PATENT DOCUMENTS

| | | |
|---|---|---|
| 5,075,511 A | 12/1991 | Li |
| 5,414,152 A | 9/1995 | Cipullo |
| 6,673,737 B2 | 1/2004 | Mehnert et al. |
| 7,820,866 B2 | 10/2010 | Fetsko et al. |
| 7,858,830 B2 | 12/2010 | Evitt et al. |
| 8,674,135 B2 | 3/2014 | Davis, Jr. |
| 2005/0215833 A1 | 9/2005 | Neumann et al. |
| 2005/0222467 A1 | 10/2005 | Kodama et al. |
| 2008/0051480 A1 | 2/2008 | Terajima et al. |
| 2012/0010434 A1 | 1/2012 | Tsutsuminai et al. |
| 2012/0310014 A1 | 12/2012 | Palmer et al. |
| 2012/0310015 A1 | 12/2012 | Palmer et al. |
| 2014/0121417 A1 | 5/2014 | Youssef et al. |

FOREIGN PATENT DOCUMENTS

WO    2012150560 A1    11/2012

OTHER PUBLICATIONS

A. C. Cole, J. L. Jensen, I. Ntai, K. L. T. Tran, K. J. Weave, D. C. Forbes, J. H. Davis Jr. 2002. "Novel Bronsted Acidic Ionic Liquids and Their Use as Duel Solvent-Catalysts." J. Am. Chem. Soc. 124: 5962.
A. Riisager, R. Fehrmann, M. Haumann, B. S. K. Gorle, P. Wasserscheid. 2005. "Stability and Kinetic Studies of Supported Ionic Liquid Phase Catalysts for Hydroformylation of Propene." Ind. Eng. Chem. Res. 44 (26): 9853.
C. DeCastro, E. Sauvage, M.H. Valkenberg, W.F. Holderich. 2000. "Immobilised Ionic Liquids as Lewis Acid Catalysts for the Alkylation of Aromatic Compounds with Dodecene." Journal of Catalysis 196 (1): 86.
C. E. Song, M. Y. Yoon, D. S. Choi. 2005. "Significant Improvement of Catalytic Efficiencies in Ionic Liquids." Bulletin of the Korean Chemical Society 26 (9): 1321.
D. Yin, C. Li, L. Tao, N. Yu, S. Hu, D. Yin. 2006. "Synthesis of diphenylmethane derivatives in Lewis acidic ionic liquids." Journal of Molecular Catalysis A: Chemical 245 (1-2): 260.
J. Gui, X. Cong, D. Liu, X. Zhang, Z. Hu, Z. Sun. 2004. "Novel Brønsted acidic ionic liquid as efficient and reusable catalyst system for esterification." Catalysis Communications 5 (9): 473.
J. Sun, S.-I. Fujita, M. Arai. 2005. "Development in the green synthesis of cyclic carbonate from carbon dioxide using ionic liquids." Journal of Organometallic Chemistry 690 (15): 3490.
J. Sun, W. Cheng, W. Fan, Y. Wang, Z. Meng, S. Zhang. 2009. "Reusable and efficient polymer-supported task-specific ionic liquid catalyst for cycloaddition of epoxide with CO2." Catalysis Today 148 (3-4): 361.
K. Matuszek, A. Chrobok, F. Coleman, K. R. Seddon, M. Swadźba-Kwaśny. 2014. "Tailoring ionic liquid catalysts: structure, acidity and catalytic activity of protonic ionic liquids based on anionic clusters, [(HSO4)(H2SO4)x]-(x = 0, 1, or 2)." Green Chemistry 16 (7): 3463.
M. D. Sliger, S. J. P'Pool, R. K. Traylor, J. McNeill III, S. H. Young, N. W. Hoffman, M. A. Klingshim, R. D. Rogers, K. H. Shaughnessy. 2005. "Promoting effect of ionic liquids on ligand substitution reactions." Journal of Organometallic Chemistry 690 (15): 3540.
M. H. Valkenberg, C. deCastro, W. F. Holderich. 2001. "Friedel-Crafts acylation of aromatics catalysed by supported ionic liquids." Applied Catalysis A: General 215 (1-2): 185.
M. Yoshizawa, M. Hirao, K. Ito-Akita, H. Ohno. 2001. "Ion conduction in zwitterionic-type moltensalts and their polymers." J. Mater. Chem. 11 (4): 1057.

(Continued)

*Primary Examiner* — Sikarl A Witherspoon
(74) *Attorney, Agent, or Firm* — Roberts Calderon Safran & Cole P.C.

(57) ABSTRACT

A catalyst system useful in the production of bisphenol-A comprises (a) an acidic heterogeneous catalyst; (b) a first catalyst promoter comprising at least one organic sulfur-containing compound; and (c) a second catalyst promoter different from the first catalyst promoter and comprising at least one organic Brønsted acidic ionic compound.

14 Claims, No Drawings

(56) References Cited

OTHER PUBLICATIONS

P. Wasserscheid, T. Welton. 2002. Ionic Liquid in Synthesis. Edited by T. Welton P. Wasserscheid. Weinheim: Wiley-VCH.
Q. Wu, M. Wang, Y. Hao, H. Li, Y. Zhao, Q. Jiao. 2014. "Synthesis of Polyoxymethylene Dimethyl Ethers Catalyzed by Brønsted Acid Ionic Liquids with Alkanesulfonic Acid Groups." Ind. Eng. Chem. Res. 53 (42): 16254.
Y. Du, F. Tian. 2005. "Brønsted Acidic Ionic Liquids as Efficient and Recyclable Catalysts for Protection of Carbonyls to Acetals and Ketals Under Mild Conditions." Synthetic Communications 35 (20): 2703.
Y. Xiao, S. V. Malhotra. 2005. "Friedel-Calls acylation reactions in pyridinium based ionic liquids." Journal of Organometallic Chemistry 690 (15): 3609.
Y. Zhao, J. Long, F. Deng, X. Liu, Z. Li, C. Xia, J. Peng. 2009. "Catalytic amounts of Brønsted acidic ionic liquids promoted esterification: Study of acidity-activity relationship." Catalysis Communications 10 (5): 732.
Z. Duan, Y. Gu, J. Zhang, L. Zhu, Y. Deng. 2006. "Protic pyridinium ionic liquids: Synthesis, acidity determination and their performances for acid catalysis." Journal of Molecular Catalysis A: Chemical 260 (1-2): 163.
A. S. Amarasekara, B. Wiredu. 2014. "Sulfonic Acid Group Functionalized Ionic Liquid Catalyzed Hydrolysis of Cellulose in Water: Structure Activity Relationships." Sustainable Energy 2 (3): 102.
H. Arasawaa, C. Odawaraa, R. Yokoyamaa, H. Saitohb, T. Yamauchia, N. Tsubokawab. 2004. "Grafting of zwitterion-type polymers onto silica gel surface and their properties." Reactive and Functional Polymers 61 (2): 153.
H. Li, P. S. Bhadury, B. Song, S. Yang. 2012. "Immobilized functional ionic liquids: efficient, green, and reusable catalysts." RSC Advances 2 (33): 12525.
M. Vafaeezadeh, Z. B. Dizicheh, M. M. Hashemi. 2013. "Mesoporous silica-functionalized dual Brønsted acidic ionic liquid as an efficient catalyst for thioacetalization of carbonyl compounds in water." Catalysis Communications 41: 96.
Z. Xu, H. Wan, J. Miao, M. Han, C. Yang, G. Guan. 2010. "Reusable and efficient polystyrene-supported acidic ionic liquid catalyst for esterifications." Journal of Molecular Catalysis A: Chemical 332 (1-2): 152.
International Search Report and Written Opinion dated Jun. 28, 2018 in a corresponding application PCT/US2018/028082.

CATALYST SYSTEM AND PROCESS FOR PRODUCING BISPHENOL-A

CROSS-REFERENCE TO RELATED APPLICATIONS

The present application is a U.S. National Phase of PCT/US2018/028082 filed on Apr. 18, 2018 which claims priority to the U.S. Provisional Patent Application No. 62/489,262 filed Apr. 24, 2017. The disclosure of the PCT Application is hereby incorporated by reference into the present Application.

FIELD

This invention relates to a catalyst system and process for producing bisphenol-A.

BACKGROUND

Bisphenol-A (BPA), also referred to as 2,2-bis (4-hydroxyphenyl) propane or para, para-diphenylolpropane (p,p-BPA), is a commercially significant compound used to manufacture polycarbonates, other engineering thermoplastics and epoxy resins. The polycarbonate application in particular demands high purity BPA due to stringent requirements for optical clarity and color in the finished application. BPA is produced commercially by the condensation of acetone and phenol and, in fact, BPA production is the largest consumer of phenol. The reaction may take place in the presence of a strong homogenous acid, such as hydrochloric acid, sulfuric acid, or toluene sulfonic acid, or in the presence of a heterogeneous acid catalyst, such as a sulfonated ion exchange resin. In recent years, acidic ion exchange resins have become the overwhelming choice as catalysts for the condensation reaction of bisphenol manufacture, and strongly acidic sulfonated polystyrene ion exchange resins are particularly useful in this regard.

Two different techniques for employing heterogeneous acid catalysts in bisphenols production predominate in industrial practice. In one technique, a cocatalyst is freely circulated in the reactor with the reaction feed. It is used to enhance the selectivity and/or activity of the reaction. An organic mercaptan, such as methyl or ethyl mercaptan, or a mercaptocarboxylic acid, such as 3-mercaptopropionic acid, is typically used as the freely circulating cocatalyst in this technique. The acidic sites of the resin are left available, that is, largely unbound to the cocatalyst. This provides flexibility in adjusting the optimal concentration of cocatalyst given the particular reaction conditions in question.

In the second technique for employing heterogeneous acid catalysts in the production of bisphenols, the catalyst is modified by appending cocatalytic agents, such as thiazolidines and aminothiols, to some of the acid sites on the catalyst. For example, mercapto-promoter groups may be attached to backbone sulfonate ions of a cation exchange resin by covalent or ionic nitrogen linkages. The fixed cocatalyst technique requires less direct handling and treatment of cocatalysts than the freely circulating cocatalyst process. The ability to refine the process by differential treatment of the resin and cocatalyst is greatly reduced but there are fewer possibilities for processing problems and reaction dynamics are less complicated than is seen in the free cocatalyst technique.

Although these existing catalyst systems and processes for producing BPA are effective and are practiced commercially, there remains a strong interest in developing improved systems and processes.

SUMMARY

According to the present invention, it has now been found that the activity and/or selectivity of BPA catalyst systems based on heterogeneous acid catalyst and sulfur-containing promoters, both fixed and freely circulating, can be increased by the addition of organic Brønsted acidic ionic compounds (OBICs). In addition, these improvements can generally be obtained without sacrificing product quality. In fact, where the OBIC is a zwitterionic compound, an improvement in selectivity to the para, para-isomer may be accompanied by a reduction in color of the product. The resulting catalysts also show significant activity for other condensation reactions.

Thus, in one aspect the invention resides in a catalyst system useful in the production of bisphenol-A comprising:
(a) an acidic heterogeneous catalyst;
(b) a first catalyst promoter comprising at least one organic sulfur-containing compound; and
(c) a second catalyst promoter different from the first catalyst promoter and comprising at least one organic Brønsted acidic ionic compound.

In a further aspect, the invention resides in a process for producing bisphenol-A by the reaction of acetone and phenol in a reaction medium in the presence of a catalyst system, wherein the catalyst system comprises:
(a) an acidic heterogeneous catalyst;
(b) a first catalyst promoter comprising at least one organic sulfur-containing compound; and
(c) a second catalyst promoter different from the first catalyst promoter and comprising at least one organic Brønsted acidic ionic compound.

In one embodiment, the at least one organic Brønsted acidic ionic compound comprises a zwitterionic compound.

DETAILED DESCRIPTION

Described herein is a catalyst system comprising (a) an acidic heterogeneous catalyst, especially an ion exchange resin, (b) a first catalyst promoter comprising at least one organic sulfur-containing compound; and (c) a second catalyst promoter different from the first catalyst promoter and comprising at least one organic Brønsted acidic ionic compound. Also described herein are uses of the catalyst system in condensation reactions, such as the condensation of carbonyl compounds with phenolic compounds to produce polyphenols and especially the condensation of phenol with acetone to produce bisphenol-A (BPA).

Acidic Heterogeneous Catalyst

Known examples of acidic heterogeneous catalysts useful in condensation reactions, such as the production of BPA, include molecular sieves, salts of heteropolyacids partially neutralized and insolubilized, and strongly acidic cation exchange resins. All such catalysts have utility in the present catalyst system and process.

Suitable molecular sieves include aluminosilicate zeolites, such as ZSM-5, zeolite beta, zeolite Y and mordenite. Other molecular sieves that have been suggested as condensation catalysts include the so-called non-zeolite molecular sieves, such as aluminophosphates and metalloaluminophosphates, for example $ALPO_4$-5, SAPO-5, SAPO-II, CoAPO-5, MnAPSO-31 and TiAPSO-5. Again these find utility in the present catalyst system.

Other known heterogeneous acid condensation catalysts include partially neutralized heteropolyacids, which are obtained by substituting part of protons in a heteropolyacid by alkali metal ions or ammonium ions to form a heterogeneous solid, heteropolyacids and their salts held on a carrier such as active carbon, alumina, silica and diatomaceous earth, zeolites and layered clay compounds.

By far the best known and commercially important acidic heterogeneous catalysts for use in the production of BPA are cation exchange resins. The effectiveness of these acidic ion exchange resins in the present process is to some extent influenced by their exchange capacities such that the greater the exchange capacity, the more desirable the resin. Preferably, the cation exchange capacity is at least about 0.5 and, more preferably, greater than about 4.0 meq/g dry weight. Also, those cation exchange resins having bound cationic exchange groups of the stronger exchange potential acids are preferred for use in the present process. Acidic cation exchange resins suitable for use in the present process of the invention include sulfonated styrene-divinylbenzene copolymers, sulfonated cross-linked styrene polymers, phenol-formaldehyde-sulfonic acid resins, benzene-formaldehyde-sulfonic acid resins, perfluorinated sulfonic acid resins and the like. These include resins sold under such trade names as Amberlites or Amberlysts (Rohm and Haas Co.), DOWEX (Dow Chemical Co.), Permutit QH (Permutit Co.), Chempro (Chemical Process Co.), catalysts from Purolite, Lewatit® (LANXESS Deutschland GmbH), NAFION® (DuPont) and the like. Strong acid sulfonated styrene-divinylbenzene copolymer resins are preferred. Suitable cation exchange resins are made from sulfonated polymerized styrene monomer which has been cross linked with from about 1% to about 8% divinylbenzene (resin). Specific examples of suitable sulfonated resins are Amberlyst® 131, Lewatit® K-1221, Purolite® CT-122, Purolite® CT-124, Diaion™ SK104H, Tulsion® 38, and Dowex® 50WX4.

Organic Sulfur Promoter

The present catalyst system also includes at least one organic sulfur-containing promoter, which generally contains at least one thiol, S—H, group. Such thiol promoters can be either ionically or covalently bonded to the heterogeneous catalyst or unbound to the heterogeneous catalyst and added separately to the condensation reaction. Non-limiting examples of bound promoters include mercaptoalkylpyridines, mercaptoalkylamines, thiazolidines and aminothiols. Non-limiting examples of unbound promoters include alkyl mercaptans, such as methyl mercaptan (MeSH) and ethyl mercaptan, mercaptocarboxylic acids, such as mercaptopropionic acid, and mercaptosulfonic acids.

The amount of organic sulfur-containing promoter employed in the catalyst system depends on the particular acidic heterogeneous catalyst employed and the condensation process to be catalyzed. In general, however, the organic sulfur-containing promoter is employed in an amount from 2 to 30 mol %, such as 5 to 20 mol %, based on the acid group (sulfonic group) in the acid ion exchanger.

Organic Brønsted Acidic Ionic Compound

In addition to the acidic heterogeneous catalyst and the at least one organic sulfur-containing promoter, the present catalyst system includes a further promoter comprising at least one organic Brønsted acidic ionic compound (OBIC).

As used herein, the term "organic Brønsted acidic ionic compound" is used to mean a salt consisting of anions and cations, which exists in molten form at temperatures below 400° C., normally below 100° C., and often below 50° C., which exhibits Brønsted (proton-donating) acidity and in which one of the anions or cations has an organic moiety. The proton acidity may originate both from the cation if it contains a proton at, for example, a quarternized N atom or from the anion if it contains protons, for instance, in $HSO_4^-$ or $H_2PO_4^-$.

The organic cationic group of the organic Brønsted acidic ionic compound can include, but is not limited to, quaternary ammonium, chlolinium, sulfonium, phosphonium, guanidinium, imidazolium, imidazolinium, indolium, isoindolium, pyridinium, pyrrolinium, pyrrolidinium, pyrimidinium, morpholinium, quinolinium, isoquinolium, pyrazolium, pyrazolidinium, pyrazinium, thioazolium, thioazolidinium, isotheiazolium, isothiazolidinium oxazolium, oxazolidinium, isoxazolium, isoxazolidinium, piperazinium, diazinium, morpholinium, oxazine, thiomorpholinium, thiazinium, piperidinium, or any of the above combinations. The anionic group of the organic Brønsted acidic ionic compound can be selected from, but is also not limited to, the following strong acid conjugates: bis(pentafluoroethylsulfonyl)imide, bis(trifluoromethylsulfonyl)imide, chlorides, bromides, iodides, fluoroalkanesulfonates, tosylates, hydrogen sulfate, fluorosulfate, perchlorate, nitrate, hexafluorophosphate, hexafluoroantimonate, and tetrafluoroborate or any of their combinations.

In some embodiments, the organic Brønsted acidic ionic compound is a zwitterionic compound, namely a neutral molecule with both positive and negative electrical charges. Suitable zwitterionic compounds can be synthesized using as the starting material an alkyl sulfone, a cyclic sulfonic ester, or other hetero-atom containing compound typically containing a Group V or VI element. These hetero compounds are primarily nitrogen, phosphorous, or sulfur-containing species, with the hetero atoms likely providing the functionality for the zwitterionic compounds to anchor to the ion exchange resin catalyst. Examples of suitable hetero compounds contain at least one of the following moieties: ammonia, amine, chloline, sulfide, phosphine, phosphorine, guanidine, imidazole, imidazolidine, aniline, indole, isoindole, pyridine, piperidine, pyrimidine, quinazoline, pyrrole, pyrrolidine, quinoline, isoquinoline, pyrazole, pyrazolidine, pyrazine, thioazole, thioazolidine, isotheiazole, isothiazolidine oxazole, oxazolidine, isoxazole, isoxazolidine piperazine, diazine, morpholine, oxazine, thiomorpholine, thiazine moiety, and their derivatives.

The amount of organic Brønsted acidic ionic compound employed in the catalyst system depends on the particular acidic heterogeneous catalyst employed and the condensation process to be catalyzed. In general, however, the Brønsted acidic ionic compound is added in an amount from 30 to 100 mol % relative to the amount of acid sites on the catalyst.

Use of the Catalyst System in Condensation Reactions

The catalysts system described above is found to have activity in condensation reactions, particularly condensation reactions between a carbonyl compound reactant and a phenolic compound reactant to produce a polyphenol product. Examples of suitable carbonyl compounds are those compounds represented by the following formula:

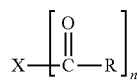

wherein R represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated; n is greater than 0, preferably from 1 to 3, more preferably from 1-2, and most preferably is 1; and when n is greater than 1, X represents a bond, or a multivalent linking group having from 1 to 14 carbon atoms, preferably from 1 to 6 carbon atoms, more preferably from 1 to 4 carbon atoms; and when n is 1, X represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated, provided that X and R are not both hydrogen.

Suitable carbonyl compounds for use herein include aldehydes and ketones. These compounds generally contain from three to fourteen carbon atoms, and are preferably aliphatic ketones. Examples of suitable carbonyl compounds include ketones such as acetone, methyl ethyl ketone, diethyl ketone, dibutyl ketone, isobutyl methyl ketone, acetophenone, methyl and amyl ketone, cyclohexanone, 3,3,5-trimethylcyclohexanone, cyclopentanone, 1,3-dichloroacetone and the like. The most preferred is acetone.

The carbonyl compounds are reacted with phenolic compounds. Phenolic compounds are aromatic compounds containing an aromatic nucleus to which is directly bonded at least one hydroxyl group. Phenolic compounds suitable for use herein include phenol and the homologues and substitution products of phenol containing at least one replaceable hydrogen atom directly bonded to the aromatic phenol nucleus. Such groups substituting for the hydrogen atom and directly bonded to the aromatic nucleus include the halogen radicals such as chloride and bromide, and the hydrocarbon radicals such as alkyl, cycloalkyl, aryl, alkaryl and aralkyl groups. Suitable phenolic compounds include phenol, the cresols, the xylenols, carvacrol, cumenol, 2-methyl-6-ethyl phenol, 2,4-dimethyl-3-ethylphenol, o-chlorophenol, m-chlorophenol, o-t-butylphenol, 2,5-xylenol, 2,5-di-t-butylphenol, o-phenylphenol, 4-ethylphenol, 2-ethyl-4-methylphenol, 2,3,6-trimethylphenol, 2-methyl-4-tert-butylphenol, 2-tertbutyl-4methylphenol, 2,3,5,6-tetramethylphenols, 2,6-dimethylphenol, 2,6-ditertbutylphenol, 3,5-dimethylphenol, 2-methyl-3,5-diethylphenol, o-phenylphenol, p-phenylphenol, naphthols, phenanthrol, and the like. Most preferred are compositions comprising phenol. Mixtures of any of the above may be used.

The above is not meant to limit the invention but to illustrate representative examples of carbonyl compounds and phenolic compounds which are known in the art to make desirable polyphenol and for which those of skill in the art can substitute other similar reactants.

In the preparation of the polyphenols, an excess of the phenolic compound reactant over the carbonyl compound reactant is usually desirable. Generally at least about 2, preferably from about 4 to about 25, moles of phenolic compound per mole of carbonyl compound is desirable for high conversion of the carbonyl compound. Solvents or diluents are not necessary in the process of the present invention for the manufacture of the polyphenol except at low temperature.

The polyphenol compounds obtained by the condensation reaction of a phenolic compound and a carbonyl compound in the present process are compounds wherein the nuclei of at least two phenolic radicals are directly attached by carbon to carbon linkages to the same single carbon atom in the alkyl group. An illustrative non-limiting example of a polyphenol compound is represented by the formula:

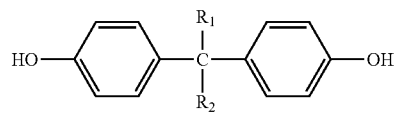

wherein $R_1$ and $R_2$ each independently represent a monovalent organic radical. Examples of such radicals include hydrocarbon radicals such as aliphatic, cycloaliphatic, aromatic, or heterocyclic, more specifically hydrocarbon radicals, such as alkyl, cycloalkyl, aryl, aralkyl, or alkaryl, whether saturated or unsaturated. Preferably, $R_1$ and $R_2$ each independently represent an alkyl radical having from 1 to 2 carbon atoms. Most preferably, the polyphenol compound comprises 2,2-bis (4-hydroxyphenyl) propane, i.e. bisphenol-A (BPA).

The reaction conditions used to effect the condensation reaction described above will vary depending on the type of phenolic compound, solvent, carbonyl compound, and condensation catalyst selected. Generally, the phenolic compounds and the carbonyl compounds are reacted in a reaction vessel, whether in the batch or continuous mode, at a temperature ranging from about 20° C. to about 130° C., preferably from about 50° C. to about 90° C.

The pressure conditions are not particularly limited and the reaction may proceed at atmospheric, sub atmospheric or super atmospheric pressure. However, it is preferred to run the reaction either without any externally induced pressure, or at sufficient pressure to force the reaction mixture across a catalyst bed or to force the reaction mixture upstream in a vertical reactor, or to maintain the contents of the reaction vessel in a liquid state if the reaction is run at a temperature above the boiling point of any ingredient. The pressure and temperature should be set under conditions to retain the reactants in the liquid phase in the reaction zone. The temperature may exceed 130° C., but should not be so high as to degrade any of the ingredients in the reaction vessel, nor should it be so high as to degrade the reaction product or promote the synthesis of a substantial amount of unwanted by-products.

The reactants are introduced into the reaction zone under conditions to assure a molar excess of the phenolic compound over the carbonyl compound. Preferably, the phenolic compound is reacted in a substantial molar excess over the carbonyl compound. For example, the molar ratio of the phenolic compound to the carbonyl compound is preferably at least about 2:1, more preferably at least about 4:1, and up to about 25:1.

Where the unbound thiol promoter is methyl mercaptan, and the carbonyl compound is acetone, 2,2-bis(methylthio) propane (BMTP) is formed in the presence of an acidic catalyst. In the presence of a hydrolyzing agent, BMTP dissociates in the reaction zone into methyl mercaptan and acetone as acetone is condensed with phenol to form BPA. A convenient hydrolyzing agent is water, which may be introduced into any of the feed charges, directly into the reaction zone, or may be produced in situ by the condensation reaction between the carbonyl compound and the phenolic compound. A molar ratio of water to BMTP catalyst promoter ranging from about 1:1 to about 5:1 is sufficient to adequately hydrolyze the BMTP catalyst promoter. This quantity of water is produced in situ under typical reaction conditions. Thus, additional water does not need to be introduced into the reaction zone, although water may optionally be added if desired.

Any suitable reactor may be used as the reaction zone. The reaction can occur in a single reactor, or in a plurality of reactors connected in series or in parallel. The reactor can be a back mixed or plug flow reactor, and the reaction can be conducted in a continuous or batch mode, and the reactor can be oriented to produce an up-flow or down-flow stream. In the case of the fixed bed flow system, the liquid space velocity of the mixture of the raw materials supplied to the reactor is usually 0.2 to 50 $hr^{-1}$. In the case of the suspended bed batch system, the amount of the strongly acid ion exchange resin used, although variable depending on the reaction temperature and pressure, is usually 20 to 100% by weight based on the mixture of the raw materials. The reaction time is usually 0.5 to 5 hours.

Any method known to those of skill in the art may be employed to recover the polyphenol compound. Generally, however, the crude reaction mixture effluent from the reaction zone is fed to a separator, such as a distillation column. The polyphenol product, polyphenol isomers, unreacted phenolic compound, and a small amount of various impurities are removed from the separator as a bottoms product. This bottoms product may be fed to a further separator. While crystallization is a common method of polyphenol separation, any known method of separating polyphenol from the bottoms product or mother liquor can be used depending upon the desired degree of purity of the polyphenol product. Once separated, the mother liquor comprising phenol and polyphenol isomers may be returned to the reaction zone as reactants.

The invention will now be more particularly described with reference to the following non-limiting Examples.

Examples 1 to 12

A series of condensation reaction experiments were conducted to investigate the addition of various organic Brønsted acidic ionic compounds to the condensation of phenol and acetone in the presence of a thiol-promoted ion exchange resin catalyst. The experiments were carried out in a batch reactor system comprising a 500-ml three-necked jacketed round bottom flask, a two-stage (40° C. followed by 2° C.) condenser to minimize the loss of volatile components, and an ethylene glycol circulating bath for temperature control of the reaction mixture. A thermocouple was inserted into the reactor to monitor the reaction temperature throughout the experiments. The temperature of the reaction mixture was maintained at approximately 75° C. by circulating the glycol through the reactor jacket. However, in some experiments, the reactor temperature was lowered to 70° C. instead to investigate the temperature effect. The reactor was preloaded with 184 grams of phenol, 8 grams of p,p-BPA isomer, and 4 grams of commercial mother liquor (ML) and 5 dried grams of a commercial ion exchange resin catalyst. All reactions were performed under a nitrogen blanket and with constant stirring of the reactor medium. The p,p-BPA isomer and mother liquor were obtained from commercially operated BPA plants.

The ion exchange resin catalyst used in the experiments was Purolite® CT-122, a commercial, 2% crosslinked, gel type, styrene-divinylbenzene (S-DVB) based sulfonic acid ion exchange resin. The resin catalyst was water washed, air dried, and subsequently dried with phenol before its use.

The organic Brønsted acidic ionic compounds (OBICs) employed in the experiments were as follows:
1-Ethyl-3-methylimidazolium trifluoromethanesulfonate (EMIM TFA)
1-Ethyl-3-methylimidazolium methanesulfonate (EMIM MSA)
1-Ethyl-3-methylimidazolium hydrogen sulfate (EMIM HSA)
1-Butyl-3-methylimidazolium trifluoromethanesulfonate (BMIM TFA)
Tetraethylammonium trifluoromethanesulfonate (TEA TFA)
Tetrabutylammonium methanesulfonate (TBA MSA)
1-Butyl-1-methylpyrrolidinium trifluoromethanesulfonate (BMPD TFA)
4-(3-trimethylsily-1-limidazolio)-1-butanesulfonic acid (TMSIM BSA)

One of the above compounds, TMSIM BSA, was synthesized in-house using a previously published protocol, see A. C. Cole, J. L. Jensen, I. Ntai, K. L. T. Tran, K. J. Weaver, D. C. Forbes, J. H. Davis Jr. 2002. "Novel Brønsted Acidic Ionic Liquids and Their Use as Dual Solvent-Catalysts." J. Am. Chem. Soc. 124: 5962. The remainder of the compounds listed above were purchased from Sigma-Aldrich and Alfa Aesar and were used as received.

In each experiment, the ion exchange resin catalyst in an unpromoted form and an organic Brønsted acidic ionic compound were charged to the phenol/p,p-BPA/ML mixture between 14 to 18 hours prior to the start of the reaction (i.e. before the addition of acetone and thiol promoter) for conditioning. The mixture was stirred continuously during conditioning to allow the resin catalyst and reaction mixture to equilibrate. The molar amount of the organic Brønsted acidic ionic compounds added in these experiments was generally equal to or less than the equivalent of the sulfonic acids on the IER catalyst. The water content of the reaction medium was analyzed and subsequently adjusted to the desired water concentration level (approximately 0.5% wt or 1.1% wt) prior to starting each experiment. The amounts of acetone and 2,2-bis(methylthio)propane (BMTP), a thiol promoter, used in each experiment were approximately 9.8 gm and 2.8 gm, respectively.

A sample was taken from the reactor prior to the addition of the acetone and BMTP and at specific intervals throughout each experiment to analyze reactor composition. The samples were prepared according to internal standard protocols and then analyzed by high performance liquid chromatography (HPLC), and gas chromatographs with flammable ionization detector (GC/FID) and thermal conductivity detector (GC/TCD) to determine water content, acetone conversion, and p,p-BPA selectivity. The reaction rates of each individual experiment were compared using the acetone conversion obtained 30 minutes after the reaction began. The results are shown in Table 1 which also gives the results for the following comparative experiments:

Comparison A in which the ion exchange resin catalyst and BMTP promoter were tested without addition of any organic Brønsted acidic ionic compound to establish a baseline case.

Comparison B in which the homogeneous acid catalyst p-toluene sulfonic acid (PTSA) and BMTP promoter were tested without addition of any organic Brønsted acidic ionic compound.

Comparison C in which the homogeneous acid catalyst ethanesulfonic acid (ESA) and BMTP promoter were tested without addition of any organic Brønsted acidic ionic compound.

Comparison D in which 1-ethyl-3-methylimidazolium trifluoromethanesulfonate (EMIM TFA) was tested alone.

Comparison E in which 1-ethyl-3-methylimidazolium hydrogen sulfate (EMIM HSA) was tested alone.

Comparison F in which tetraethylammonium trifluoromethanesulfonate (TEA TFA) was tested alone.

TABLE 1

| Example | OBIC (gm) | Reactor Temp. (° C.) | Initial water level (wt %) | Acetone conv, % | ppBPA select., % |
|---------|-----------|----------------------|----------------------------|-----------------|------------------|
| A | — | 75 | 0.48 | 70.5 | 93.2 |
| B | — | 75 | 1.09 | 92.4 | 92.8 |
| C | — | 75 | 1.10 | 81.7 | 94.2 |
| D | EMIM TFA 6.9 | 75 | 0.45 | — | — |
| E | EMIM HSA 5.4 | 75 | 0.45 | — | — |
| F | TEA TFA 7.3 | 75 | 0.45 | — | — |
| 1 | EMIM TFA 6.8 | 75 | 0.46 | 97.9 | 91.9 |
| 2 | EMIM TFA 2.2 | 75 | 0.46 | 95.0 | 92.5 |
| 3 | EMIM TFA 2.3 | 70 | 1.12 | 74.0 | 93.9 |
| 4 | EMIM TFA 2.4 | 75 | 1.12 | 83.2 | 93.4 |
| 5 | EMIM HSA 1.8 | 75 | 1.11 | 80.6 | 93.1 |
| 6 | EMIM MSA 1.8 | 75 | 1.11 | 67.3 | 93.4 |
| 7 | TEA TFA 2.5 | 75 | 1.11 | 83.8 | 93.4 |
| 8 | TEA TFA 2.5 | 70 | 1.11 | 77.5 | 93.9 |
| 9 | BMIM TFA 2.5 | 75 | 1.11 | 84.8 | 93.2 |
| 10 | BMPD TFA 2.5 | 75 | 1.14 | 84.6 | 93.3 |
| 11 | TBA MSA 2.9 | 75 | 1.11 | 71.7 | 93.6 |
| 12 | TMSIM BSA 7.2 | 75 | 0.47 | 85.8 | 93.3 |

For the baseline case, Comparison A, acetone conversion was approximately 71% after 30 minutes of reaction and the corresponding the p,p-BPA selectivity was about 93%. Not surprisingly, the homogeneous acid catalyst p-toluene sulfonic acid (PTSA), Comparison B, was much more active but slightly less selective than the IER catalyst. The acetone conversion of PTSA exceeded 92% even with a higher initial water concentration of 1.1 wt %. As expected, ethanesulfonic acid (ESA), Comparison C, being a weaker acid than PTSA converted 82% of the acetone under the same conditions. With Comparisons D to F, little or no change in reactor composition were observed even after testing for up to 4 hours.

Referring to the other results summarized in Table 1, the trifluoromethanesulfonate (triflate or TFA) based OBICs appeared to offer a surprisingly significant boost to the activity of the IER catalyst. Thus, in Example 1, with the addition of 6.8 gm of EMIM TFA, in the presence of the ion exchange resin and thiol promoter, and at conditions similar to the baseline case, i.e. 75° C. and 0.5% water level, the acetone conversion reached 98% after 30 minutes of reaction time. The conversion was only reduced slightly to 95% in Example 2 after the quantity of the EMIM TFA was cut to 2.3 gm, equivalent to one-third of the sulfur acid group on the IER. The acetone conversion with EMIM TFA was further reduced to 74%, thus approaching the baseline value of 71%, only after the initial water level was raised to 1.1% and the reaction temperature lowered from 75 to 70° C. (Example 3). For purpose of comparison, subsequent experiments with the other OBICs were mostly performed at reaction temperature of 75° C., initial water level of 1.1 wt %, and OBIC quantity equivalent to one-third of the sulfur acid group on the IER catalyst.

Similar performance patterns were observed with the other TFA based OBICs including TEA TFA (Example 7), BMIM TFA (Example 9), and BMPD TFA (Example 10), with an acetone conversion of 83.8%, 84.8%, and 84.6%, respectively. Likewise, at initial water concentration of 1.1 wt % and temperature of 70° C., the acetone conversion with TEA TFA was about 78% (Example 8). Hence, the cationic group of the OBIC appeared to have less influence on the observed activity enhancement in these cases.

EMIM HSA also provided strong activity improvement. The acetone conversion of EMIM HSA at 75° C. and 1.1% water level was 80.6% (Example 5) which was a few percent lower than those of the TFA based OBICs, but significantly higher compared to the baseline case. On the other hand, under the same conditions TBA MSA only showed slight to moderate increase relative to the baseline (Example 11). Overall, these results suggest that the activity enhancement is a strong function of the quantity of the OBIC and the acid strength of the conjugate of its anionic group.

The use of a zwitterionic compound, TMSIM BSA, consisting of a bulky cationic group, also resulted in a notable increase of resin catalyst activity, with 85.8% acetone conversion achieved in Example 12 after 30 minutes of reaction time and with the same initial water level (0.5%) as the baseline case.

Examples 13 to 36

The process of the preceding Examples was repeated with the following commercially purchased zwitterionic compounds (ZICs):
4-(3-Butyl-1-imidazolio)-1-butanesulfonate (BIM BSA)
3-(Benzyldimethylammonio)propanesulfonate (BDA PSA)
3-(Cyclohexylamino)-1-propanesulfonic acid (CAPS)
3-(Cyclohexylamino)-2-hydroxy-1-propanesulfonic acid (CAPSO)
3-(N-Morpholino)propanesulfonic acid (MOPS)
3-Morpholino-2-hydroxypropanesulfonic acid (MOPSO)
3-(1-Pyridinio)-1-propanesulfonate (3PPS)
N-[Tris(hydroxymethyl)methyl]-3-aminopropanesulfonic acid (TAPS)
3-(N,N-Bis[2-hydroxyethyl]amino)-2-hydroxypropanesulfonic acid (DIPSO)
N-(1,1-Dimethyl-2-hydroxyethyl)-3-amino-2-hydroxypropanesulfonic acid (AMPSO)
2-(4-Pyridyl)ethanesulfonic acid (4PES)
2-(Cyclohexylamino)ethanesulfonic acid (CHES)
and the following ZICs synthesized in-house:
4-(3-Butyl-1-imidazolio)-1-butanesulfonate (BIM BSA)
3-(3-Butyl-1-imidazolio)-1-propanesulfonate (BIM PSA)
3-(2,3-Dimethyl-1-imidazolio)-1-propanesulfonate (DMIM PSA)
4-(2,3-Dimethyl-1-imidazolio)-1-butanesulfonate (DMIM BSA)
3-(3-Trifluoroacetyl-1-imidazolio)-1-propanesulfonate (TFAIM PSA)
3-(4-Ethyl-1-pyridinio)-1-propanesulfonate (4EP PSA)
3-(4-Tertbutyl-1-pyridinio)-1-propanesulfonate (4TBP PSA)
3-(2-Ethyl-1-pyridinio)-1-propanesulfonate (2EP PSA)

The results of the tests are summarized in Table 2, which also provides the data for the baseline case, Comparison A. The results were mostly measured at an acetone conversion of 85 to 90%.

TABLE 2

| Example | ZIC (gm) | Reactor Temp (° C.) | Initial water level (wt %) | ppBPA select., % | op/pp |
|---------|----------|---------------------|----------------------------|------------------|-------|
| A | — | 75 | 0.48 | 93.2 | 0.038 |
| 13 | BIM BSA 6.7 | 70 | 0.46 | 94.7 | 0.029 |

TABLE 2-continued

| Example | ZIC (gm) | Reactor Temp (° C.) | Initial water level (wt %) | ppBPA select., % | op/pp |
|---|---|---|---|---|---|
| 14 | BIM BSA 3.3 | 75 | 0.47 | 94.0 | 0.035 |
| 15 | BIM BSA 6.7 | 75 | 0.46 | 94.2 | 0.032 |
| 16 | CAPS 5.9 | 75 | 0.46 | 93.5 | 0.037 |
| 17 | CAPSO 6.2 | 75 | 0.50 | 93.8 | 0.036 |
| 18 | MOPS 5.5 | 75 | 0.46 | 93.3 | 0.037 |
| 19 | MOPSO 6.0 | 75 | 0.46 | 93.9 | 0.035 |
| 20 | CHES 5.3 | 75 | 0.46 | 93.4 | 0.039 |
| 21 | TAPS 6.3 | 75 | 0.47 | 93.7 | 0.034 |
| 22 | DIPSO 6.5 | 75 | 0.47 | 94.1 | 0.034 |
| 23 | AMPSO 6.0 | 75 | 0.46 | 93.9 | 0.034 |
| 24 | 3PPS 5.4 | 75 | 0.46 | 94.1 | 0.034 |
| 25 | 4PES 4.9 | 75 | 0.47 | 94.1 | 0.034 |
| 26 | 4PES 4.9 | 75 | 1.11 | 94.5 | 0.035 |
| 27 | BDA PSA 6.7 | 75 | 0.44 | 94.0 | 0.036 |
| 28 | BIM BSA* 6.9 | 75 | 0.46 | 94.3 | 0.034 |
| 29 | BIM PSA* 6.5 | 75 | 0.47 | 94.1 | 0.035 |
| 30 | DMIM PSA* 5.8 | 75 | 0.44 | 94.1 | 0.035 |
| 31 | DMIM BSA* 6.1 | 75 | 0.46 | 94.2 | 0.032 |
| 32 | 4EP PSA* 6.2 | 75 | 0.47 | 93.6 | 0.039 |
| 33 | DMIM BSA* 6.2 | 70 | 0.93 | 94.9 | 0.032 |
| 34 | 4TBP PSA* 6.8 | 75 | 0.46 | 93.9 | 0.038 |
| 35 | 2EP PSA* 6.1 | 75 | 0.46 | 93.8 | 0.038 |
| 36 | TFAIM PSA* 7.5 | 75 | 0.46 | 93.6 | 0.037 |

*Synthesized in-house

As shown in Table 2, the combinations of a ZIC, the ion exchange resin catalyst, and a thiol promoter such as 2,2-bis(methylthio)propane (BMTP) consistently exhibited improved p,p-BPA selectivity compared to that of the baseline case. The observed selectivity improvement also seemed to correlate with the quantity of ZIC addition. The p,p-BPA selectivity dropped slightly from 94.2% to 94.0% and the o,p-BPA and p,p-BPA isomer ratio increased from 0.32 to 0.35 after the quantity of 4-(3-Butyl-1-imidazolio)-1-butanesulfonate (BIM BSA) was reduced from 6.7 in Example 15 to 3.3 gm in Example 14. The selectivity improved further after the reaction temperature was reduced from 75 to 70° C. in Example 13. Both purchased and synthesized versions of BIM BSA also showed similar performance in their experiments.

Most of the ZICs showed some increase in p,p-BPA selectivity and reduction in the isomer ratio of o,p-BPA to p,p-BPA, which can be beneficial in downstream purification. The addition of a hydroxyl group on the ZIC appeared to be advantageous for further selectivity improvement as evident in the cases of CAPS vs CAPSO and MOPS vs MOPSO. Other similar ZICs such as AMPSO and DIPSO, also performed well. It was also noted that the ZICs with longer alkyl chain sulfonic acid group seemed to perform slightly better (DMIM PSA vs DMIM BSA, BIM PSA vs. BIM BSA, and CHES vs. CAPS). The cationic group of the ZIC likely also contributed to the performance difference among the ZICs evaluated. Nonpolar substitute (alkyl vs. trifluoroacetyl) on the cationic group of the ZICs appeared slightly more favorable (TFAIM PSA vs BIM PSA).

The most improved p,p-BPA selectivity was however realized by addition of BIM BSA, dimethylimidazolium butane sulfonate (DMIM BSA), or 2-(4-pyridyl)ethanesulfonic acid (4PES). The p,p-BPA selectivity of the 4PES also increased further from 94.1 to 94.5% after the initial water level was raised from 0.5 to 1.1 wt %. These improvements constituted a selectivity increase of greater than 1% from the baseline case (Comparison A). The ratio of o,p-BPA to p,p-BPA (op/pp) isomer was also reduced to as low as 0.029 relative to the baseline value of 0.038. The combination of lower reactor temperature and/or higher initial water level also further improved the p,p-BPA selectivity by up to 1.7% in the case of DMIM BSA compared to that of the baseline case (~93.2%).

Example 37

In certain of the tests conducted in Examples 13 to 36, the color of the reaction medium was determined qualitatively, by visual assessment during sampling for HPLC and GC analyses. Samples collected from the reaction medium for the base (IER only) case typically have exhibited a light brownish orange color. Surprisingly, a pale to light yellow color of the reaction medium was achieved through the use of imidazolium-based ZICs. The color reduction of the BPA reaction medium was particularly noticeable during batch experiments conducted with zwitterionic compounds DMIM PSA and DMIM BSA.

The invention claimed is:

1. A catalyst system useful in the production of bisphenol-A comprising:
    (a) an acidic heterogeneous catalyst comprising an ion exchange resin;
    (b) a first catalyst promoter comprising at least one organic sulfur-containing compound; and
    (c) a second catalyst promoter different from the first catalyst promoter and comprising at least one organic Bronsted acidic ionic compound.

2. The catalyst system of claim 1, wherein the acidic heterogeneous catalyst comprises a sulfonated ion exchange resin.

3. The catalyst system of claim 1, wherein the at least one organic sulfur-containing compound is selected from the group consisting of an alkyl mercaptans, mercaptocarboxylic acids, mercaptosulfonic acids, mercaptoalkylpyridines, mercaptoalkylamines, thiazolidines and aminothiols.

4. The catalyst system of claim 1, wherein the at least one organic Bronsted acidic ionic compound is a liquid at 25° C.

5. The catalyst system of claim 1, wherein the at least one organic Bronsted acidic ionic compound comprises a zwitterionic compound.

6. A process for producing bisphenol-A by the reaction of acetone and phenol in a reaction medium in the presence of a catalyst system, wherein the catalyst system comprises:
    (a) an acidic heterogeneous catalyst;
    (b) a first catalyst promoter comprising at least one organic sulfur-containing compound; and
    (c) a second catalyst promoter different from the first catalyst promoter and comprising at least one organic Bronsted acidic ionic compound.

7. The process of claim 6, wherein the acidic heterogeneous catalyst comprises an ion exchange resin.

8. The process of claim 6, wherein the acidic heterogeneous catalyst comprises a sulfonated ion exchange resin.

9. The process of claim 6, wherein the at least one organic sulfur-containing compound is selected from the group consisting of an alkyl mercaptans, mercaptocarboxylic acids, mercaptosulfonic acids, mercaptoalkylpyridines, mercaptoalkylamines, thiazolidines and aminothiols.

10. The process of claim 6, wherein the at least one organic Bronsted acidic ionic compound is a liquid at 25° C.

11. The process of claim 6, wherein the at least one organic Bronsted acidic ionic compound comprises a zwitterionic compound.

12. The process of claim 6, wherein at least one of the first and second catalyst promoters is bound to the acidic heterogeneous catalyst.

13. The process of claim 6, wherein at least one of the first and second catalyst promoters is added to the reaction medium separately from the acidic heterogeneous catalyst.

14. A catalyst system useful in the production of bisphenol-A comprising:
   (a) an acidic heterogeneous catalyst comprising a sulfonated ion exchange resin;
   (b) a first catalyst promoter comprising at least one organic sulfur-containing compound; and
   (c) a second catalyst promoter different from the first catalyst promoter and comprising at least one organic Bronsted acidic ionic compound which comprises a cation having a quaternized N-atom or is a zwitterionic compound.

* * * * *